United States Patent
Brady et al.

(10) Patent No.: US 9,192,662 B2
(45) Date of Patent: Nov. 24, 2015

(54) METHODS USING IMMUNOMODULATORY COMPOUNDS FOR MODULATING LEVEL OF CD59

(75) Inventors: Helen A. Brady, San Diego, CA (US); Kyle Chan, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 1718 days.

(21) Appl. No.: 12/362,411

(22) Filed: Jan. 29, 2009

(65) Prior Publication Data

US 2009/0317385 A1 Dec. 24, 2009

Related U.S. Application Data

(60) Provisional application No. 61/063,011, filed on Jan. 29, 2008.

(51) Int. Cl.
*A61K 31/454* (2006.01)
*A61K 39/395* (2006.01)

(52) U.S. Cl.
CPC ............ *A61K 39/395* (2013.01); *A61K 31/454* (2013.01)

(58) Field of Classification Search
CPC .................................... A61K 31/454
USPC ........................................ 514/183
See application file for complete search history.

(56) References Cited

U.S. PATENT DOCUMENTS

| | | | |
|---|---|---|---|
| 6,316,471 B1 * | 11/2001 | Muller et al. | 514/323 |
| 2003/0045552 A1 | 3/2003 | Robarge et al. | |
| 2004/0220144 A1 * | 11/2004 | Zeldis | 514/58 |
| 2005/0143420 A1 * | 6/2005 | Moutouh-de Parseval et al. | 514/323 |
| 2006/0084695 A1 * | 4/2006 | Griffin et al. | 514/422 |
| 2007/0116710 A1 | 5/2007 | Bell et al. | |
| 2008/0220003 A1 * | 9/2008 | Schnatbaum et al. | 424/178.1 |

FOREIGN PATENT DOCUMENTS

| | | |
|---|---|---|
| WO | WO 03/087392 | 10/2003 |
| WO | WO 03/097052 A2 * | 11/2003 |
| WO | WO 2005/055929 | 6/2005 |
| WO | WO 2005/112928 | 12/2005 |
| WO | WO 2007/139939 | 12/2007 |

OTHER PUBLICATIONS

List et al. NEJM, 2005, vol. 352, pp. 549-557.*
Bessler, XP002525853, retrieved from http://hematology.wssd.edu/conferences/presentations/bessler931607 ppt (2007).
Nakao et al., *International Journal of Hematology*, 82(5): 412-416 (2005).

* cited by examiner

*Primary Examiner* — James D Anderson
(74) *Attorney, Agent, or Firm* — Jones Day

(57) ABSTRACT

Provided herein are methods of treating, preventing or managing disorders associated with low CD59 levels. The methods encompass the administration of an immunomodulatory compound provided herein, such as 3-(4-amino-1-oxo-1,3-dihydro-isoindol-2-yl)-piperidine-2,6-dione or 1,3-dioxo-2-(2,6-dioxopiperidin-3-yl)-4-aminoisoindoline. Further described are methods of treatment using the immunomodulatory compounds in combination with other therapeutic agents or therapies. Pharmaceutical compositions and single unit dosage forms suitable for use in the methods provided herein are also disclosed.

3 Claims, 3 Drawing Sheets

METHODS USING IMMUNOMODULATORY COMPOUNDS FOR MODULATING LEVEL OF CD59

This application claims priority to U.S. Provisional Application No. 61/063,011, filed Jan. 29, 2008. the entirety of which is incorporated herein by reference.

1. FIELD

Provided herein are methods of treating, preventing or managing diseases associated with CD59 deficiency, including hemolytic diseases such as, for example, paroxysmal nocturnal hemoglobinuria ("PNH") by administering an immunomodulatory compound. Exemplary immunomodulatory compounds include, for example, 3-(4-amino-1-oxo-1,3-dihydro-isoindol-2-yl)-piperidine-2,6-dione, which is also known as lenalidomide and 4-amino-2-(2,6-dioxopiperidin-3-yl)isoindoline-1,3-dione, also known as CC-4047 or pomolidomide.

In one embodiment, the methods and compositions provided herein encompasses the use of specific combinations or "cocktails" of lenalidomide and other therapy, such as treatment with steroids, blood transfusions, anti-coagulation therapy, bone marrow transplantation and combinations thereof. Also provided are pharmaceutical compositions and dosing regimens with the immunomodulatory compounds.

2. BACKGROUND

Paroxysmal nocturnal hemoglobinuria ("PNH") is a blood disorder wherein red blood cells are compromised and are thus destroyed more rapidly than normal red blood cells. PNH results from a mutation of bone marrow cells resulting in the generation of abnormal blood cells. More specifically, PNH is believed to be a disorder of hematopoietic stem cells, which give rise to distinct populations of mature blood cells. The basis of the disease is believed to be somatic mutations leading to the inability to synthesize the glycosyl-phosphatidylinositol ("GPI") anchor that is responsible for binding proteins to cell membranes. The mutated gene, PIG-A (phosphatidylinositol glycan class A), resides in the X chromosome and can have several different mutations, varying from deletions to point mutations.

PNH causes a sensitivity to complement proteins, which occurs in the cell membrane. PNH cells are deficient in a number of proteins. For example, PNH cells are associated with deficiencies in essential complement-regulating surface proteins. These complement-regulating surface proteins include the decay-accelerating factor ("DAF") also known as CD55 and membrane inhibitor of reactive lysis ("MIRL") also known as CD59.

CD59 deficiencies have also been described in the literature to have potential roles in the pathophysiology of the disease including ischemia-reperfusion injury (Yamada et. al. *J Immun.* 2004; Omidvar et. al. *J Immun.* 2006, Turnberg et al *Amer. J of Pathology* 2004) and autoimmune disease, such as lupus erythematosis and rheumatoid arthritis (Kinderlerer et al. *Arhritis Research & Therapy* 2006, Alahlafi et. al. *J Cutaneous Pathology* 2005).

There is a continuing need for efficient methods and compositions that can be used to treat, prevent or manage diseases associated with CD59 deficiency, including hemolytic diseases such as, for example, PNH.

3. SUMMARY

In one embodiment, provided herein are methods of treating, preventing or managing diseases associated with CD59 deficiency, including hematologic diseases, such as, for example, paroxysmal nocturnal hemoglobinuria (PNH).

In another embodiment, provided herein are methods for up-regulating the levels of CD59. In certain embodiments, the levels of CD59 are up-regulated by more than about 10%, 20%, 30%, 40%, 50%, 60%, 70%, 80%, 90%, 95% or more. In certain embodiments, the levels of CD59 are up-regulated by stimulating gene expression (e.g., transcription and translation). In certain embodiments, methods of treating preventing or managing ischemic-reperfusion injury and autoimmune disease, such as lupus erythematosis and rheumatoid arthritis are provided.

In another aspect, a method of increasing the proportion of complement sensitive type III red blood cells in total red blood cell content in a patient afflicted with a hemolytic disease is contemplated. In certain embodiments, increasing the proportion of complement sensitive type III red blood cells results in increase in the total red blood cell count in a patient afflicted with a hemolytic disease. In certain embodiments, the proportion of complement sensitive type III red blood cells in increased by more than about 10%, 20%, 30%, 40%, 50%, 60%, 70%, 80%, 90%, 95% or more. By increasing type III red blood cell count, symptoms such as fatigue and anemia also can be alleviated in a patient afflicted with a hemolytic disease. Thus, in certain embodiments, provided herein are methods for treating fatigue in a subject afflicted with a hemolytic disease.

In another embodiment provided herein is a method of treating thrombosis. In yet another aspect, provided herein is a method of treating a subject afflicted with a hemolytic disease by administering: 1) one or more compounds known to increase hematopoiesis (for example, either by boosting production, eliminating stem cell destruction or eliminating stem cell inhibition) in combination with 2) an immunomodulatory compound provided herein. Suitable compounds known to increase hematopoiesis include, for example, steroids, immunosuppressants (such as, cyclosporine), anti-coagulants (such as, warfarin), folic acid, iron and the like, erythropoietin (EPO) and antithymocyte globulin (ATG) and antilymphocyte globulin (ALG). In certain embodiments, erythropoietin (EPO) (a compound known to increase hematopoiesis) is administered in combination with an anti-C5 antibody. Examples of anti-C5 antibodies include, but are not limited to eculizumab, h5G1.1-mAb, h5G1.1-scFv and other functional fragments of h5G1.1.

The methods comprise administering to a patient a therapeutically or prophylactically effective amount of an immunomodulatory compound provided herein, or a pharmaceutically acceptable salt, solvate (e.g., hydrate), stereoisomer, clathrate, or prodrug thereof.

In another embodiment, an immunomodulatory compound provided herein is administered in combination with a therapy conventionally used to treat, prevent or manage symptoms associated with the deficiency of CD59, including hemolysis and thrombosis. Examples of such conventional therapies include, but are not limited to, treatment with steroids, blood transfusions, anti-coagulation therapy, bone marrow transplantation and combinations thereof.

Also provided are pharmaceutical compositions, single unit dosage forms, and dosing regimens which comprise an immunomodulatory compound provided herein, or a pharmaceutically acceptable salt, solvate (e.g., hydrate), stereoisomer, clathrate, or prodrug thereof, and a second, or additional, active agent or ingredient. Second active agents or ingredients include specific combinations, or "cocktails," of drugs or therapy, or both.

In one embodiment, the compound to be used in the methods and compositions is 3-(4-amino-1-oxo-1,3-dihydro-isoindol-2-yl)-piperidine-2,6-dione (lenalidomide), 4-amino-2-(2,6-dioxopiperidin-3-yl)isoindoline-1,3-dione or N-{[2-(2,6-dioxo(3-piperidyl)-1,3-dioxoisoindolin-4-yl]methyl}cyclopropyl-carboxamide.

4. BRIEF DESCRIPTION OF DRAWINGS

5. DETAILED DESCRIPTION

Figure 1:
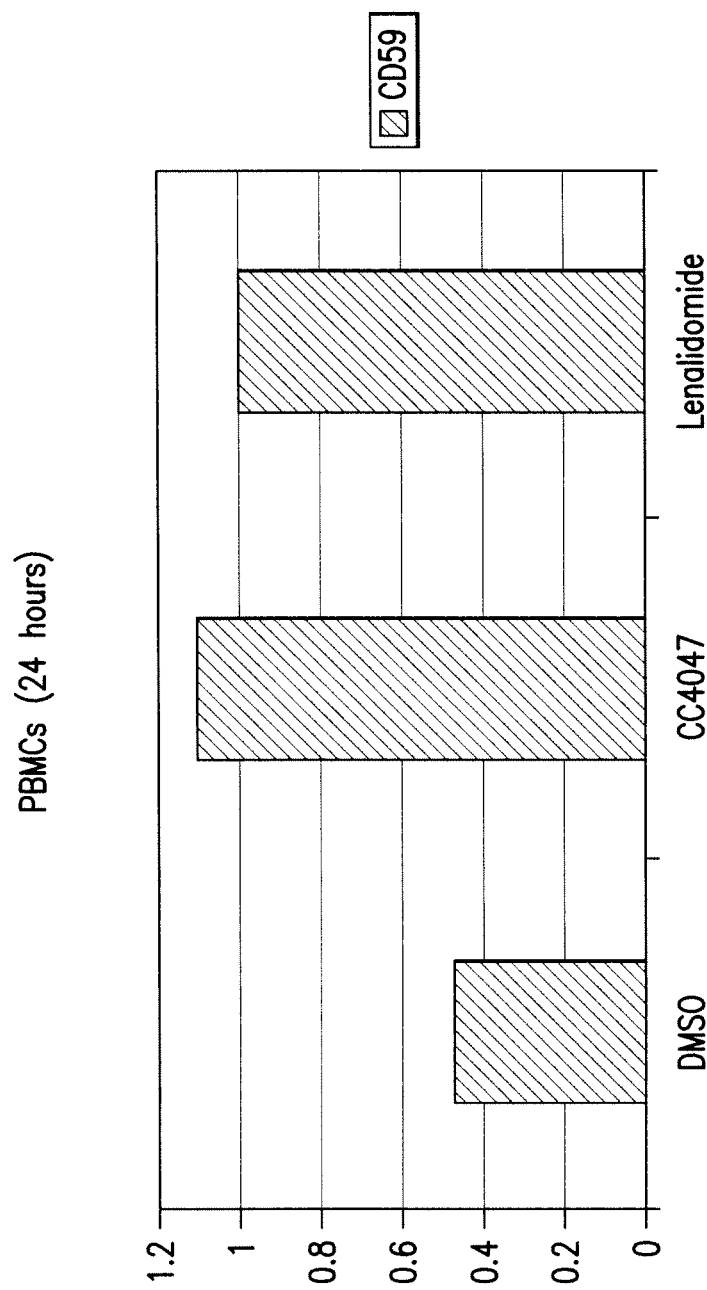
FIG. 1 illustrates increase in CD59 mRNA levels in peripheral blood mononuclear cells after treatment with exemplary immunomodulatory compounds, lenalidomide and CC-4047.

In certain embodiments, provided herein are methods of up-regulating the levels of CD59 by administering a therapeutically or prophylactically effective amount of an immunomodulatory compound provided herein, or a pharmaceutically acceptable salt, solvate (e.g., hydrate), stereoisomer, clathrate, or prodrug thereof. In one embodiment, provided herein are methods encompassing treatment, prevention or management of hemolytic diseases associated with CD59, including paroxysmal nocturnal hemoglobinuria (PNH), ischemic-reperfusion injury and autoimmune disease. In certain embodiments, the autoimmune disease is selected from lupus erythematosis and rheumatoid arthritis.

5.1 Immunomodulatory Compounds

As used herein and unless otherwise indicated, the terms "immunomodulatory compounds" encompass certain small organic molecules that inhibit LPS induced monocyte TNF-α, IL-1β, IL-12, IL-6, MIP-1α, MCP-1, GM-CSF, G-CSF, and/or COX-2 production, including those known as "IMiDs®" (Celgene Corporation). Specific immunomodulatory compounds are discussed below.

TNF-α is an inflammatory cytokine produced by macrophages and monocytes during acute inflammation. TNF-α is responsible for a diverse range of signaling events within cells. Without being limited by a particular theory, one of the biological effects exerted by the immunomodulatory compounds provided herein is the reduction of myeloid cell TNF-α production. Immunomodulatory compounds of provided herein may enhance the degradation of TNF-α mRNA.

Further, without being limited by theory, immunomodulatory compounds used herein may also be potent co-stimulators of T cells and increase cell proliferation dramatically in a dose dependent manner. Immunomodulatory compounds provided herein may also have a greater co-stimulatory effect on the CD8+ T cell subset than on the CD4+ T cell subset. In addition, the compounds, in certain embodiments, have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds used herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-di-oxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6-dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. patent publication no. 2003/0096841 published on May 22, 2003, and International Application No. PCT/US01/50401 (International Publication No. WO 02/059106). The entireties of each of the patents and patent applications identified herein are incorporated herein by reference. Immunomodulatory compounds do not include thalidomide.

Various immunomodulatory compounds provided herein contain one or more chiral centers, and can exist as racemic mixtures of enantiomers or mixtures of diastereomers. The methods and compositions herein encompass the use of stereomerically pure forms of such compounds, as well as the use of mixtures of those forms. For example, mixtures comprising equal or unequal amounts of the enantiomers of a particular immunomodulatory compounds may be used in methods and compositions provided herein. These isomers may be asymmetrically synthesized or resolved using standard techniques such as chiral columns or chiral resolving agents. See, e.g., Jacques, J., et al. *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In one embodiment, immunomodulatory compounds provided include, but are not limited to, 1-oxo-and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

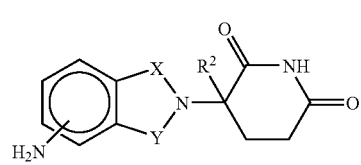

in which one of X and Y is C=O, the other of X and Y is C=O or CH$_2$, and R$^2$ is hydrogen or lower alkyl, in particular methyl. Specific immunomodulatory compounds include, but are not limited to:

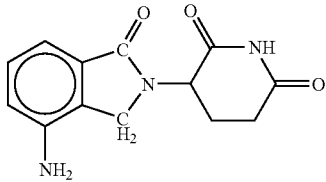

1-oxo-2-(2,6-dioxopiperidin-3-yl)-4-aminoisoindoline;

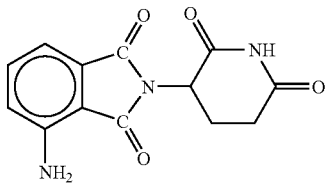

1,3-dioxo-2-(2,6-dioxopiperidin-3-yl)-4-aminoisoindoline; and

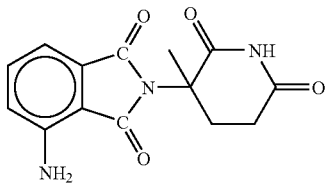

1,3-dioxo-2-(3-methyl-2,6-dioxopiperidin-3-yl)-4-aminoisoindole, and optically pure isomers thereof. The compounds can be obtained via standard, synthetic methods (see e.g., U.S. Pat. No. 5,635,517, incorporated herein by reference). The compounds are also available from Celgene Corporation, Warren, N.J.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, greater than about 90% by weight of one enantiomer of the compound and less than about 10% by weight of the other enantiomers of the compound, greater than about 95% by weight of one enantiomer of the compound and less than about 5% by weight of the other enantiomers of the compound, greater than about 97% by weight of one enantiomer of the compound and less than about 3% by weight of the other enantiomers of the compound or greater than about 99% by weight of one enantiomer of the compound and less than about 1% by weight of the other enantiomers of the compound.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

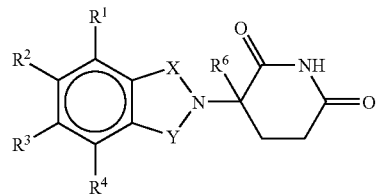

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.

Compounds representative of this class are of the formulas:

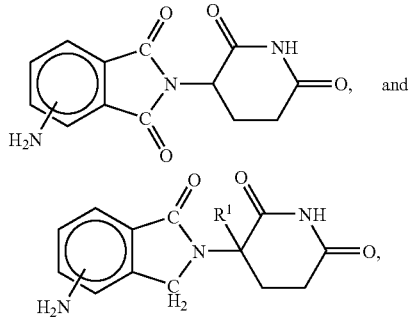

wherein R$^1$ is hydrogen or methyl. In a separate embodiment, the methods and compositions provided herein encompass the use of enantiomerically pure forms (e.g. optically pure (R) or (S) enantiomers) of these compounds.

Still other specific immunomodulatory compounds belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

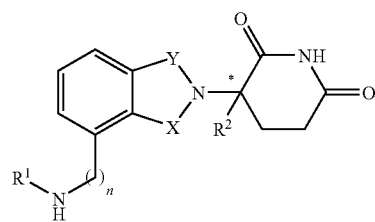

II and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^3$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^3$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl)-$C_1-C_6$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl, $(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-N$(R^6)_2$; $(C_0-C_8)$alkyl-NH—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$ alkyl or benzyl.

In other specific compounds of formula II, $R^1$ is H, $(C_1-C_8)$alkyl, benzyl, $CH_2OCH_3$, $CH_2CH_2OCH_3$, or

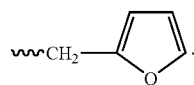

In another embodiment of the compounds of formula II, $R^1$ is

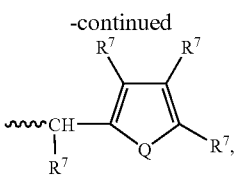

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II, $R^3$ is $(C_0-C_4)$ alkyl $C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O) NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide; and N-{[2-(2,6-dioxo(3-piperidyl))-1,3-dioxoisoindolin-4-yl]methyl}(benzylamino) carboxamide.

Still other specific immunomodulatory compounds belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

III and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

* represents a chiral-carbon center.

Other representative compounds are of formula:

wherein:

one of X and Y is C=O and the other of X and Y is C=O or $CH_2$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzo, chloro, or fluoro;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—; and $R^{10}$ is hydrogen, alkyl of to 8 carbon atoms, or phenyl.

Other representative compounds are of formula:

in which one of X and Y is C=O and the other of X and Y is C=O or $CH_2$;

each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and $R^6$ is hydrogen, alkyl of 1 to 8 carbon atoms, benzo, chloro, or fluoro.

Other representative compounds are of formula:

in which:

one of X and Y is C=O and the other of X and Y is C=O or $CH_2$;

(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen, alkyl of 1 to 8 carbon atoms, or CO—$R^7$—$CH(R^{10})NR^8R^9$ in which each of $R^7$, $R^8$, $R^9$, and $R^{10}$ is as herein defined; and $R^6$ is alkyl of 1 to 8 carbon atoms, benzo, chloro, or fluoro.

Specific examples of the compounds are of formula:

NHCO—$R^7$—$CH(R^{10})NR^8R^9$ in which:

one of X and Y is C=O and the other of X and Y is C=O or $CH_2$;

$R^6$ is hydrogen, alkyl of 1 to 8 carbon atoms, benzyl, chloro, or fluoro;

$R^7$ is m-phenylene, p-phenylene or —$(C_nH_{2n})$— in which n has a value of 0 to 4; each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S— or —NH—; and $R^{10}$ is hydrogen, alkyl of 1 to 8 carbon atoms, or phenyl.

Other specific immunomodulatory compounds include, but are not limited to, 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

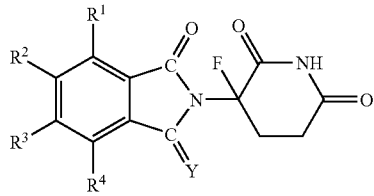

wherein:

Y is oxygen or H2 and each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds include, but are not limited to, the tetra substituted 2-(2,6-dioxopiperidin-3-yl)-1-oxoisoindolines described in U.S. Pat. No. 5,798,368, which is incorporated herein by reference. Representative compounds are of formula:

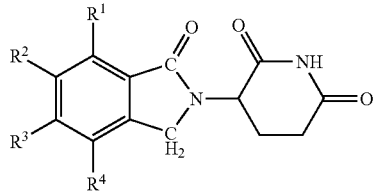

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

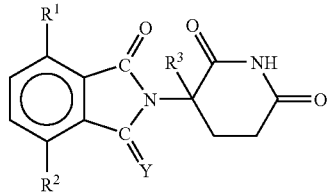

in which

Y is oxygen or $H_2$, a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and $R^3$ is hydrogen, alkyl, or benzyl.

Specific examples of the compounds are of formula:

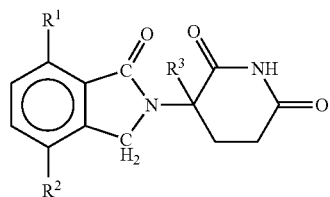

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

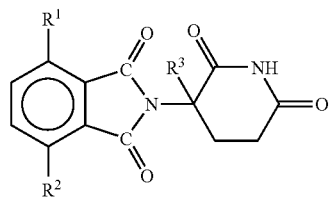

wherein:

a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl.

Other specific immunomodulatory compounds include, but are not limited to, 1-oxo and 1,3-dioxoisoindolines substituted in the 4- or 5-position of the indoline ring described in U.S. Pat. No. 6,380,239 and co-pending U.S. application publication no. 20060084815, published Apr. 20, 2006, which are incorporated herein by reference. Representative compounds are of formula:

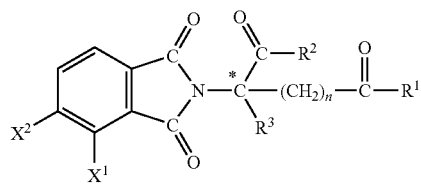

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

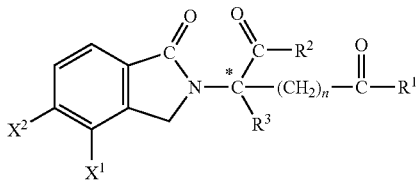

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

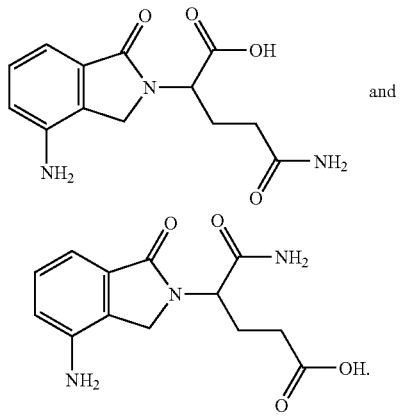

Other representative compounds are of formula:

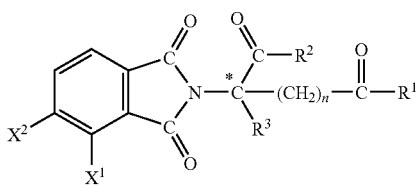

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

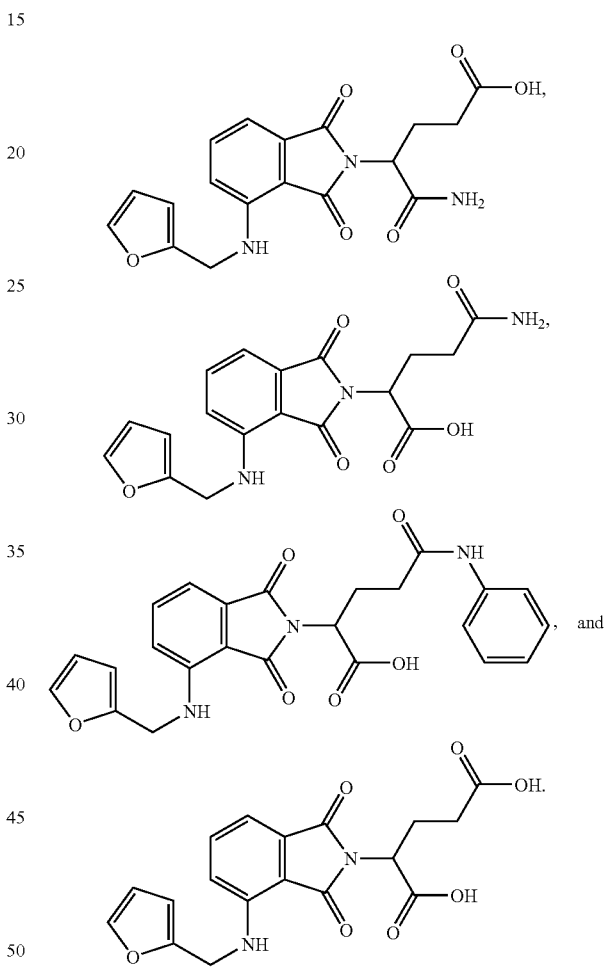

Other specific examples of the compounds are of formula:

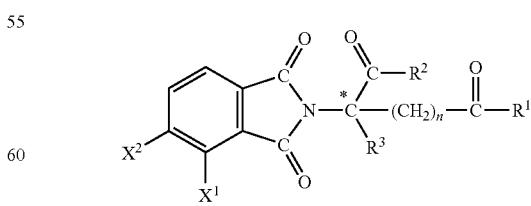

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —$COR^2$ and —$(CH_2)_nCOR^1$ are different, the carbon atom designated C* constitutes a center of chirality.

Other representative compounds are of formula:

wherein:

one of $X^1$ and $X^2$ is alkyl of one to six carbons;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —$COR^2$ and —$(CH_2)_nCOR^1$ are different, the carbon atom designated C constitutes a center of chirality.

Still other specific immunomodulatory compounds include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

wherein:

the carbon atoms designated * constitute centers of chirality;

X is —C(O)— or —$CH_2$—;

$R^1$ is alkyl of 1 to 8 carbon atoms or —$NHR^3$;

$R^2$ is hydrogen, alkyl of 1 to 8 carbon atoms, or halogen; and $R^3$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which $R^4$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Compounds used herein may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2 Definitions

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds that comprise —NO, —$NO_2$, —ONO, or —$ONO_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

The immunomodulatory compound for use in the methods and compositions contains a chiral center, and thus can exist as a racemic mixture of R and S enantiomers. The methods and compositions provided herein encompass the use of stereomerically pure forms of this compound, as well as the use of mixtures of those forms. For example, mixtures comprising equal or unequal amounts of the enantiomers may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, or greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. In other words, the methods provided herein encompass the use of the R or S enantiomer of the immunomodulatory compound.

As used herein, unless otherwise specified, the term "treating" refers to the administration of a compound provided herein, or other additional active agent, after the onset of symptoms of the particular disease. As used herein, unless otherwise specified, the term "preventing" refers to the treatment with or administration of an immunomodulatory compound prior to the onset of symptoms, particularly to patients at risk of a disease associated with deficiency of CD59, such as paroxysmal nocturnal hemoglobinuria (PNH). The term "prevention" includes the inhibition of a symptom of the particular disease. Patients with familial history of a disease associated with deficiency of CD59 or PNH in particular are candidates for preventive regimens in certain embodiments. As used herein and unless otherwise indicated, the term "managing" encompasses preventing the recurrence of a disease associated with deficiency of CD59 in a patient who had suffered from it and/or reducing mortality rates of the patients.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Second Active Agents

An immunomodulatory compound can be used with or combined with other pharmacologically active compounds ("second active agents or ingredients") in methods and compositions provided herein. It is believed that certain combinations work synergistically in the methods provided herein. Immunomodulatory compounds can also work to alleviate adverse effects associated with certain second active agents, and some second active agents can be used to alleviate adverse effects associated with immunomodulatory compounds of the invention.

One or more second active ingredients or agents can be used in the methods and compositions provided herein together with an immunomodulatory compound. Second active agents can be large molecules (e.g., proteins) or small molecules (e.g., synthetic inorganic, organometallic, or organic molecules).

In certain embodiment, the second active agents are steroids such as prednisone to suppress hemolysis. In other embodiments, the second active agents are anticoagulants to prevent clot formation.

In one embodiment, the immunomodulatory compounds provided herein can be administered in combination with one or more compounds known to increase hematopoiesis (for example, either by boosting production, eliminating stem cell destruction or eliminating stem cell inhibition). Suitable compounds known to increase hematopoiesis include, for example, steroids, immunosuppressants (such as, cyclosporin), anti-coagulants (such as, warfarin), folic acid, iron and the like, erythropoietin (EPO) and antithymocyte globulin (ATG) and antilymphocyte globulin (ALG). In certain embodiment, the second agent is an anti-C5 antibody selected from the group consisting of eculizumab, h5G1.1-mAb, h5G1.1-scFv and other functional fragments of h5G1.1. In certain embodiment, the anti-C5 antibody is eculizumab.

In one embodiment, the treatment of haemolytic PNH involves the use of an immunomodulatory compound provided herein in combination with folic acid which the bone marrow needs to make red blood cells. Patients who have low blood iron levels (usually assessed by the ferritin level), because they pass a lot of iron out into their urine, may require iron tablets. Patients who have severe anaemia with symptoms may need occasional or regular blood transfusions.

5.4 Methods of Treatments and Prevention

Provided herein are methods for up-regulating the levels of CD59. In certain embodiments, the levels of CD59 are up-regulated by stimulating gene expression (e.g., transcription and translation). In certain embodiments, the levels of CD59 are up-regulated by more than about 10%, 20%, 30%, 40%, 50%, 60%, 70%, 80%, 90% or more as determined by methods known in the art as well as those described herein. Further provided are methods of treating, preventing or managing diseases associated with CD59 deficiency, including hematologic diseases, such as, for example, paroxysmal nocturnal hemoglobinuria (PNH).

In one embodiment, provided are methods of treating, preventing or managing ischemic-reperfusion injury. Ischemia-reperfusion injury (IRI) is the primary cause of acute renal failure and is a predominant cause of tissue damage in conditions such as stroke, myocardial infarction, cardiopulmonary bypass, and intestinal ischemia. The role of the complement system as an important mediator of renal IRI has been demonstrated in numerous animal studies. CD59 deficient mice display upregulation of membrane attack complex and considerably more sensitive to IRI. In certain embodiments, the methods of treating, preventing or managing ischemic-reperfusion injury by upregulating the levels of CD59 are provided.

In one embodiment, provided are methods of treating, preventing or managing autoimmune hemolytic anemia. Without being limited by a particular theory, it is believed that autoimmune hemolytic anemia (AIHA) can result from complement-mediated lysis by autoantibodies and is found in some patients secondary to systemic lupus erythematosus (SLE). Studies comparing CD59 levels in red blood cells of SLE patients with and without secondary AIHA to patients with primary AIHA or normal volunteers have shown a decrease in CD59 in SLE plus AIHA patients but not in the other patient groups. In certain embodiments, provided herein are methods of treating, preventing or managing autoimmune hemolytic anemia by upregulating the levels of CD59.

In certain embodiments, methods of treating preventing or managing autoimmune disease, such as lupus erythematosis and rheumatoid arthritis are provided.

In one embodiment, provided herein are methods of treating one or more symptoms associated with PNH and other hemolytic diseases provided herein. Such symptoms include, for example, abdominal pain, fatigue, dyspnea and insomnia. Without being limited by a particular theory, symptoms can be the direct result of lysis of red blood cells (e.g., hemoglobinuria, anemia, fatigue, low red blood cell count, etc.) or the symptoms can result from low nitric oxide (NO) levels in the patient's bloodstream (e.g., abdominal pain, erectile dysfunction, dysphagia, thrombosis, etc.). It has recently been reported that almost all patients with greater than 40% PNH type III granulocyte clone have thrombosis, abdominal pain, erectile dysfunction and dysphagia, indicating a high hemolytic rate (see, Moyo et al., *British J. Haematol.* 126: 133-138 (2004)).

In certain embodiments, the methods provided herein encompass prevention, treatment or management of hemolytic diseases including symptoms such as hemoglobinuria, anemia, hemoglobinemia, dysphagia, fatigue, erectile dysfunction, recurrent abdominal pain and thrombosis associated with paroxysmal nocturnal hemoglobinuria. In certain embodiment, provided herein are methods of treating hemolysis associated with paroxysmal nocturnal hemoglobinuria in a patient afflicted with a hemolytic disease. In certain embodiments, treating hemolysis means that the duration of time a person suffers from hemolysis is reduced by about 5%, 10%, 15%, 20%, 25%, 30%, 35%, 40%, 50% or more using any method known in the art. In certain embodiments, treating hemolysis means that the intensity of hemolysis is reduced by about 5%, 10%, 15%, 20%, 25%, 30%, 35%, 40%, 50% or more using any method known in the art.

In certain embodiments, treating hemoglobinuria means a reduction in the number of times a person has red, brown, or darker urine, wherein the reduction is typically about 5%, 10%, 15%, 20%, 25%, 30%, 35%, 40%, 50% or more as determined by any method known in the art. Hemoglobinuria is a symptom resulting from the inability of a patient's natural levels of haptoglobin to process all the free hemoglobin released into the bloodstream as a result of intravascular hemolysis. Without being bound by any particular theory, it is believed that by reducing the lysis of red blood cells, the methods provided herein reduce the amount of free hemoglobin in the bloodstream and urine thereby treating hemoglobinuria.

In one aspect, a method of treating fatigue associated with paroxysmal nocturnal hemoglobinuria and other hemolytic diseases is contemplated. In one embodiment, treating fatigue means the duration of time a person suffers from fatigue is reduced by about 5%, 10%, 15%, 20%, 25%, 30%, 35%, 40%, 50% or more as determined by any method known in the art. In one embodiment, treating fatigue means the intensity of fatigue is reduced by about 5%, 10%, 15%, 20%, 25%, 30%, 35%, 40%, 50% or more as determined by any method known in the art. Without being bound by any particular theory, it is believed that fatigue is a symptom associated with intravascular hemolysis, as the fatigue relents when hemoglobinuria resolves even in the presence of anemia. In one embodiment, the methods provided herein treat fatigue by reducing the lysis of red blood cells.

In another aspect, a method of treating abdominal pain associated with paroxysmal nocturnal hemoglobinuria and other hemolytic diseases is contemplated. In one embodiment, treating abdominal pain means the duration of time a person suffers from abdominal pain is reduced by about 5%, 10%, 15%, 20%, 25%, 30%, 35%, 40%, 50% or more as determined by any method known in the art. In one embodiment, treating abdominal pain means the intensity of abdominal pain is reduced by about 5%, 10%, 15%, 20%, 25%, 30%, 35%, 40%, 50% or more as determined by any method known in the art. Without being bound by any particular theory, it is believed that abdominal pain is a symptom resulting from the inability of a patient's natural levels of haptoglobin to process all the free hemoglobin released into the bloodstream as a result of intravascular hemolysis, resulting in the scavenging of nitric oxide (NO) and intestinal dystonia and spasms. In one embodiment, the methods provided herein reduce the amount of free hemoglobin in the bloodstream, thereby reducing abdominal pain, by reducing the lysis of red blood cells.

Further provided are methods of treating dysphagia associated with paroxysmal nocturnal hemoglobinuria and other hemolytic diseases. In one embodiment treating dysphagia means the duration of time a person has dysphagia attacks is reduced by about 5%, 10%, 15%, 20%, 25%, 30%, 35%, 40%, 50% or more as determined by any method known in the art. In one embodiment treating dysphagia means the intensity of dysphagia attacks is reduced by about 5%, 10%, 15%, 20%, 25%, 30%, 35%, 40%, 50% or more as determined by any method known in the art. Without being bound by any particular theory, it is believed that dysphagia is a symptom resulting from the inability of a patient's natural levels of haptoglobin to process all the free hemoglobin released into the bloodstream as a result of intravascular hemolysis, resulting in the scavenging of NO and esophageal spasms. In one embodiment, the methods provided herein treat dysphagia by reducing the lysis of red blood cells, thereby reducing the amount of free hemoglobin in the bloodstream.

In further embodiment, provided are methods of trating erectile dysfunction associated with paroxysmal nocturnal hemoglobinuria and other hemolytic diseases. Without being bound by any particular theory, it is believed that erectile dysfunction is a symptom associated with scavenging of NO by free hemoglobin released into the bloodstream as a result of intravascular hemolysis. In one embodiment, methods herein reduce the amount of free hemoglobin in the bloodstream, thereby increasing serum levels of NO and treating erectile dysfunction associated with paroxysmal nocturnal hemoglobinuria.

In still another aspect, a method of treating thrombosis associated with paroxysmal nocturnal hemoglobinuria and other hemolytic diseases is contemplated. Treating thrombosis means the duration of time a person has thrombosis attacks is reduced by about 5%, 10%, 15%, 20%, 25%, 30%, 35%, 40%, 50% or more as determined by any method known in the art. Treating thrombosis means the intensity of thrombosis attacks is reduced by about 5%, 10%, 15%, 20%, 25%, 30%, 35%, 40%, 50% or more as determined by any method known in the art. Without being bound by any particular theory, it is believed that thrombosis is a symptom associated with scavenging of NO by free hemoglobin released into the bloodstream as a result of intravascular hemolysis and/or the lack of CD59 on the surface of platelets resulting in terminal complement mediated activation of the platelet. By reducing the lysis of red blood cells, the methods provided herein reduce the amount of free hemoglobin in the bloodstream, thereby increasing serum levels of NO and treating thrombosis associated with paroxysmal nocturnal hemoglobinuria.

In further embodiment, a method of treating anemia pain associated with paroxysmal nocturnal hemoglobinuria and other hemolytic diseases is contemplated. In one embodiment, treating amenia pain means the duration of time a person has anemia pain is reduced by about 5%, 10%, 15%, 20%, 25%, 30%, 35%, 40%, 50% or more as determined by any method known in the art. In one embodiment, treating amenia pain means the intensity of anemia pain is reduced by about 5%, 10%, 15%, 20%, 25%, 30%, 35%, 40%, 50% or more as determined by any method known in the art. Without being bound by any particular theory, it is believed that anemia in hemolytic diseases results from the blood's reduced capacity to carry oxygen due to the loss of red blood cell mass. In certain embodiment, the methods provided herein assist red blood cell levels to increase by reducing the lysis of red blood cells, thereby treating anemia associated with paroxysmal nocturnal hemoglobinuria.

It has been reported in the literature that CD59 is inactivated by glycation in the presence of high concentrations of glucose or other glycating sugars, Davies et al., *Immunology.* 2005 February; 114(2):280-6. It has been further reported that glycation-induced inactivation of CD59 as a factor contributing to anaemia in type I diabetes. Therefore, provided herein are methods of treating anaemia in type I diabetes.

In another aspect, a method of increasing the proportion of complement sensitive type III red blood cells in total red blood cell content in a patient afflicted with a hemolytic disease is contemplated. In certain embodiments, the proportion of PNH type III red blood cells of the subject's total red blood cell content is increased by 5%, 10%, 15%, 20%, 25%, 30%, 35%, 40%, 50%, 75% or more as compared to that before the treatment. The proportion of PNH type III red blood cells can be determined by any method known in the art. By increasing the proportion of complement sensitive type III red blood cells, the total red blood cell count is also increased thereby treating fatigue, anemia and reducing the patient's need for blood transfusions. The reduction in transfusions can be in frequency of transfusions, amount of blood units transfused, or both.

In one embodiment, provided herein are methods of increasing red blood cell count in a patient afflicted with a hemolytic disease. In other embodiments, the methods increase red blood cell count in a patient afflicted with a hemolytic disease resulting in the proportion of PNH type III red blood cells of the subject's total red blood cell content to greater than 5%, 10%, 15%, 20%, 25%, 30%, 35%, 40%, 50%, 75% or more as compared to that before the treatment as determined by any method known in the art. In some embodiments, the methods provided herein decrease the frequency of transfusions in a patient suffering from a hemolytic disease, such as PNH, by about 5%, 10%, 15%, 20%, 25%, 30%, 35%, 40%, 50%, 75%, 80%, 90%, 95% or more as compared to that before the treatment as determined by any method known in the art.

In certain embodiment, provided herein are methods of increasing the nitric oxide (NO) levels in a patient having PNH or some other hemolytic disease. Without being bound by any particular theory, it is believed that low NO levels arise in patients suffering from PNH or other hemolytic diseases as a result of scavenging of NO by free hemoglobin released into the bloodstream as a result of intravascular hemolysis. By reducing the lysis of red blood cells, the methods provided herein reduce the amount of free hemoglobin in the bloodstream, thereby increasing serum levels of NO. In certain embodiments, the serum levels of NO are increased by about 5%, 10%, 15%, 20%, 25%, 30%, 35%, 40%, 50%, 75%, 80%, 90%, 95% or more as determined by any method known in the art. In certain embodiments, NO homeostasis is restored as evidenced by a resolution of symptoms attributable to NO deficiencies as compared to that before the treatment.

It has been reported in the literature that deficiency of CD59 enhances T cell activity, see, Longhi et al., *Trends in Immunology*, (27) 2, 2006, 102-107. In certain embodiments, the administration of the compounds provided herein can effectively down-regulate T cell activity.

In certain embodiments, the immunomodulatory compounds provided herein, such as 3-(4-amino-1-oxo-1,3-dihydro-isoindol-2-yl-piperidine-2,6-dione (lenalidomide), 4-amino-2-(2,6-dioxopiperidin-3-yl)isoindoline-1,3-dione or N-{[2-(2,6-dioxo(3-piperidyl)-1,3-dioxoisoindolin-4-yl]methyl}cyclopropyl-carboxamide, induce increase in the mRNA levels of CD59 in several in vitro cellular models in Affymetrix gene array experiments (both primary cells and cell lines). In certain aspects, this increase is found in primary T cells, primary monocytes, NK cells, cultured PBMCs from normal and CLL patients, and the Namalwa Burkitt's lymphoma cell line.

The methods comprise administering to a patient a therapeutically or prophylactically effective amount of an immunomodulatory compound provided herein, or a pharmaceutically acceptable salt, solvate (e.g., hydrate), stereoisomer, clathrate, or prodrug thereof.

In one embodiment, an immunomodulatory compound provided herein can be administered orally and in single or divided daily doses in an amount of from about 0.10 to about 150 mg/day. In another embodiment, an immunomodulatory compound may be administered in an amount from about 0.10 to 150 mg per day, from about 1 to about 50 mg per day, or from about 5 to about 25 mg per day or from about 10 to about 25 mg per day. Specific doses per day include 1, 2, 3, 4, 5, 6, 7, 8, 9, 10, 11, 12, 13, 14, 15, 16, 17, 18, 19, 20, 21, 22, 23, 24, 25,26,27,28,29, 30, 31, 32, 33, 34, 35, 36, 37, 38, 39, 40, 41, 42, 43, 44, 45, 46, 47, 48, 49 or 50 mg per day. In one embodiment, the immunomodulatory compound is 3-(4-amino-1-oxo-1,3-dihydro-isoindol-2-yl-piperidine-2,6-dione. 4-amino-2-(2,6-dioxopiperidin-3-yl)isoindoline-1,3-dione or N-{[2-(2,6-dioxo(3-piperidyl)-1,3-dioxoisoindolin-4-yl]methyl}cyclopropyl-carboxamide.

In one embodiment, an immunomodulatory compound may be administered to patients with hemolytic diseases, such as paroxysmal nocturnal hemoglobinuria, an amount of from about 1 to 50 mg per day, from about 5 to about 25 mg per day or from about 10 to about 25 mg per day. In another embodiment, an immunomodulatory compound such as 3-(4-amino-1-oxo-1,3-dihydro-isoindol-2-yl-piperidine-2,6-dione, 4-amino-2-(2,6-dioxopiperidin-3-yl)isoindoline-1,3-dione or N-{[2-(2,6-dioxo(3-piperidyl)-1,3-dioxoisoindolin-4-yl]methyl}cyclopropyl-carboxamide may be administered in an amount of about 10, 15, 20, 25 or 50 mg per day. In a another embodiment, 3-(4-amino-1-oxo-1,3-dihydro-isoindol-2-yl-piperidine-2,6-dione can be administered in an amount of about 25 mg per day.

5.4.1 Combination Therapy with a Second Active Agent

In certain embodiment, the immunomodulatory compound, or a pharmaceutically acceptable salt, solvate (e.g., hydrate), stereoisomer, clathrate, or prodrug thereof, in combination with one or more second active agents, such as, and/or in combination with blood transfusions, anti-coagulation therapy, bone marrow transplantation and combinations thereof. Examples of immunomodulatory compounds for use herein are disclosed herein (see, e.g., section 5.1). Examples of second active agents are also disclosed herein (see, e.g., section 5.3).

Administration of an immunomodulatory compound and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. In one embodiment, the immunomodulatory compound provided herein is administered orally. Typical routes of administration for the second active agents or ingredients provided herein are known to those of ordinary skill in the art. See, e.g., *Physicians' Desk Reference*, (2006).

It is further contemplated that a combination therapy can be used wherein an immunomodulatory compound provided herein is administered in combination with a regimen of known therapy for the hemolytic disease. Such regimens include administration of 1) one or more compounds known to increase hematopoiesis (for example, either by boosting production, eliminating stem cell destruction or eliminating stem cell inhibition) in combination with 2) a compound selected from a group of compounds which bind to one or more complement components, compounds which block the generation of one or more complement components and compounds which block the activity of one or more complement components. Suitable compounds known to increase hematopoiesis include, for example, steroids, immunosuppressants (such as, cyclosporin), anti-coagulants (such as, warfarin), folic acid, iron and the like, erythropoietin (EPO), immunosuppressants such as, antithymocyte globulin (ATG) and antilymphocyte globulin (ALG), EPO derivatives, and darbepoetin alfa (commercially available as Aranesp® (Aranesp® is a man-made form of EPO produced in Chinese hamster ovary (CHO) cells by recombinant DNA technology)). In certain embodiment, the combination therapy includes administration of an anti-C5 antibody selected from the group consisting of eculizumab, h5G 1.1-mAb, h5G1.1-scFv and other functional fragments of h5G1.1. In certain embodiment, the anti-C5 antibody is eculizumab.

The combined use of the immunomodulatory compounds provided herein and conventional therapy may provide a unique treatment regimen effective in certain patients. Without being limited by theory, it is believed that immunomodulatory compounds provided herein may provide additive or synergistic effects when given concurrently with other therapy.

In one embodiment, an immunomodulatory compound herein can be administered in an amount of from about 0.10 to about 150 mg, from about 1 to about 50 mg or from about 5 to about 25 mg orally and daily alone, or in combination with a second active agent disclosed herein, prior to, during, or after the use of conventional therapy.

5.5 Pharmaceutical Compositions and Dosage Forms

Pharmaceutical compositions can be used in the preparation of individual, single unit dosage forms. Pharmaceutical compositions and dosage forms provided herein comprise an immunomodulatory compound provided herein, or a pharmaceutically acceptable salt, solvate (e.g., hydrate), stereoisomer, clathrate, or prodrug thereof. Pharmaceutical compositions and dosage forms provided herein can further comprise one or more excipients.

Pharmaceutical compositions and dosage forms provided herein can also comprise one or more additional active ingredients. Consequently, pharmaceutical compositions and dosage forms herein comprise the active ingredients disclosed herein (e.g., an immunomodulatory compound and a second active agent). Examples of optional second, or additional, active ingredients are disclosed herein. (see, e.g., section 5.3).

Single unit dosage forms provided herein are suitable for oral, mucosal, parenteral (e.g., subcutaneous, intravenous, bolus injection, intramuscular, or intraarterial), topical, transdermal or transcutaneous administration to a patient. Examples of dosage forms include, but are not limited to: tablets; caplets; capsules, such as soft elastic gelatin capsules; cachets; troches; lozenges; dispersions; suppositories; powders; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed herein will vary from one another will be readily apparent to those skilled in the art. See, e.g., *Remington's Pharmaceutical Sciences,* 20th ed., Mack Publishing, Easton Pa. (2000).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, the pharmaceutical compositions and dosage forms that contain little, if any, lactose other mono- or di-saccharides are provided in certain embodiments. As used herein, the term "lactose-free" means that the amount of lactose present, if any, is insufficient to substantially increase the degradation rate of an active ingredient.

Lactose-free compositions can comprise excipients that are well known in the art and are listed, for example, in the *US. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Further encompassed are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, for example, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiment, the dosage forms comprise an immunomodulatory compound provided herein or a pharmaceutically acceptable salt, solvate (e.g., hydrate), stereoisomer, clathrate, or prodrug thereof in an amount of from about 0.10 to about 150 mg. In other embodiment, the dosage forms comprise an immunomodulatory compound provided herein or a pharmaceutically acceptable salt, solvate (e.g., hydrate), stereoisomer, clathrate, or prodrug thereof in an amount of about 0.1, 1,2.5,5,7.5, 10, 12.5, 15, 17.5,20,25,50, 100, 150 or 200 mg. In one embodiment, the dosage form comprises 3-(4-amino-1-oxo-1,3-dihydro-isoindol-2-yl)-piperidine-2,6-dione (lenalidomide) in an amount of about 1, 2.5, 5, 10, 15, 20, 25 or 50 mg. In certain embodiments, dosage forms comprise the second active ingredient in an amount of I to about 1000 mg, from about 5 to about 500 mg, from about 10 to about 350 mg, or from about 50 to about 200 mg. Of course, the specific amount of the second agent will depend on the specific agent used, the type of disease being treated or managed, and the amount(s) of an immunomodulatory compound provided herein and any optional additional active agents concurrently administered to the patient.

5.5.1 Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

In one embodiment, the dosage form is a capsule or tablet comprising 3-(4-amino-1-oxo-1,3-dihydro-isoindol-2-yl)-piperidine-2,6-dione in an amount of about 1, 2.5, 5, 10, 15, 20, 25 or 50 mg. In one embodiment, the capsule or tablet dosage form comprises 3-(4-amino-1-oxo-1,3-dihydro-isoindol-2-yl)-piperidine-2,6-dione in an amount of about 5 or 10 mg.

In certain embodiment, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In certain embodiments, the solid oral dosage form comprises an immunomodulatory compound provided herein, anhydrous lactose, microcrystalline cellulose, polyvinylpyrrolidone, stearic acid, colloidal anhydrous silica, and gelatin.

5.5.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461,6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. Thus provided herein are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., *Surgery* 88:507 (1980); Saudek et al., *N. Engl. J. Med* 321: 574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

5.5.3 Parenteral Dosage Forms

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins (see, U.S. Pat. No. 5,134,127).

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers, excipient or diluents used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of an active ingredient is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution comprising an active ingredient is an effective mode of administration. Another embodiment is a sterile aqueous or oily solution or suspension comprising an active material injected as necessary to produce the desired pharmacological effect.

Injectables are designed for local and systemic administration. Typically a therapeutically effective dosage is formulated to contain a concentration of at least about 0.1% w/w up to about 90% w/w or more or more than 1% w/w of an active ingredient to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

5.5.4 Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving the active ingredient, or a pharmaceutically acceptable salt, solvate, hydrate or prodrug thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the active ingredient. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, 5-35 mg or about 9-30 mg of lyophilized powder, is added per mL of sterile water or other suitable carrier. The precise amount depends upon the compound used. Such amount can be empirically determined.

6. EXAMPLES

Certain embodiments provided herein are illustrated by the following non-limiting example. Some examples of the increase in CD59 with exemplary immunomodulatory compounds are shown below.

6.1 Increase in CD59 mRNA levels in unstimulated Monocytes

Human PBMCs were isolated from buffy coat from three healthy volunteers using ficoll gradient centrifugation. CD14+ monocytes were isolated from each batch of PBMCs using anti-CD14 microbeads (Miltenyi). Cells were treated with 0.1% DMSO or 4-amino-2-(2,6-dioxopiperidin-3-yl) isoindoline-1,3-dione (1 µM) 1 or lenalidomide (10 µM) for 30 minutes. Thereafter the cells were either left unstimulated or stimulated with 100 ng/ml LPS and incubated for 6 hours. After the incubation period the cells were lysed in TRI reagent (Sigma) for RNA isolation. The RNAs isolated using the TRI reagent RNA isolation protocol, were column cleaned (Qiagen) and the RNAs kept separate from the donors, were pooled for cDNA synthesis. Briefly, double-stranded cDNA will be synthesized using 2-5 µg of total RNA. Biotin-labeled cRNA will be synthesized using MessageAmp aRNA kit (Ambion), 15 µg of cRNA fragmented and hybridized to each Affymetrix human UI 33A array. The above procedures will be done twice for each RNA sample to obtain replicate biotin-labeled probes. Data analysis was performed using GeneSpring (Agilent).

Figure 2:
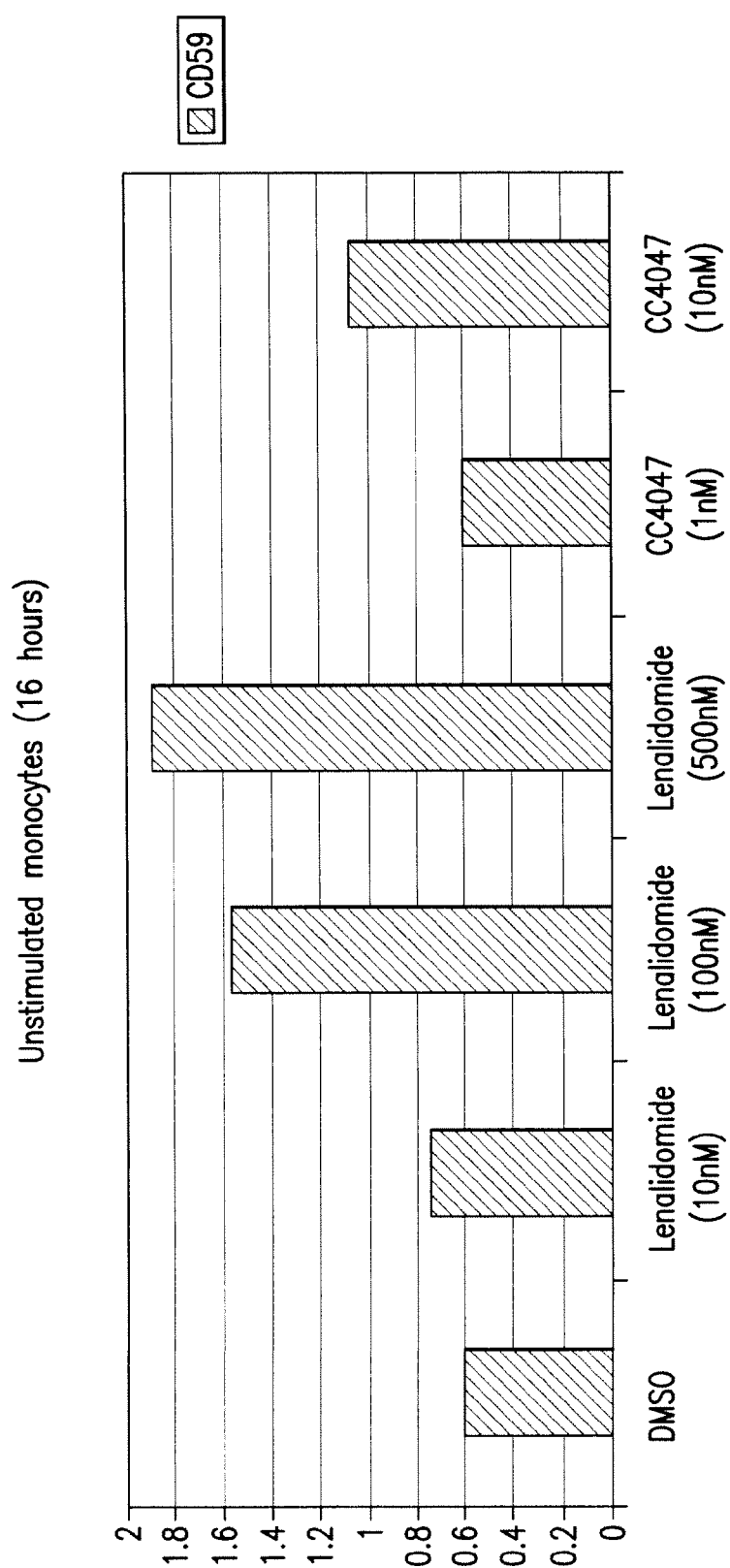
FIG. 2 illustrates increase in CD59 mRNA levels in unstimulated monocytes after treatment with exemplary immunomodulatory compounds, lenalidomide or CC-4047.

As seen in FIG. 2, CD59 mRNA levels in unstimulated monocytes show increase after treatment with 10 nM or more of 3-(4-amino-1-oxo-1,3-dihydro-isoindol-2-yl-piperidine-2,6-dione or 4-amino-2-(2,6-dioxopiperidin-3-yl)isoindoline-1,3-dione.

6.2 Increase in CD59 mRNA Levels in alpha-CD3/CD28 Stimulated T Cells

Human PBMCs were isolated from buffy coat from four healthy volunteers using ficoll gradient centrifugation CD4+ T cells were isolated from each batch of PBMCs using anti-CD4 microbeads (Miltenyi). Cells were treated with 0.1% DMSO or 4-amino-2-(2,6-dioxopiperidin-3-yl)isoindoline-1,3-dione (1 µM) 1 or lenalidomide (10 µM) in the presence or absence of anti-CD3/anti-CD28 stimulation over a time course which included 3, 6, 12 and 24 hours of treatment. Cells were harvested at indicated times and RNA isolated as described above. Methods for Affymetrix gene array analysis were as described above.

Figure 3:
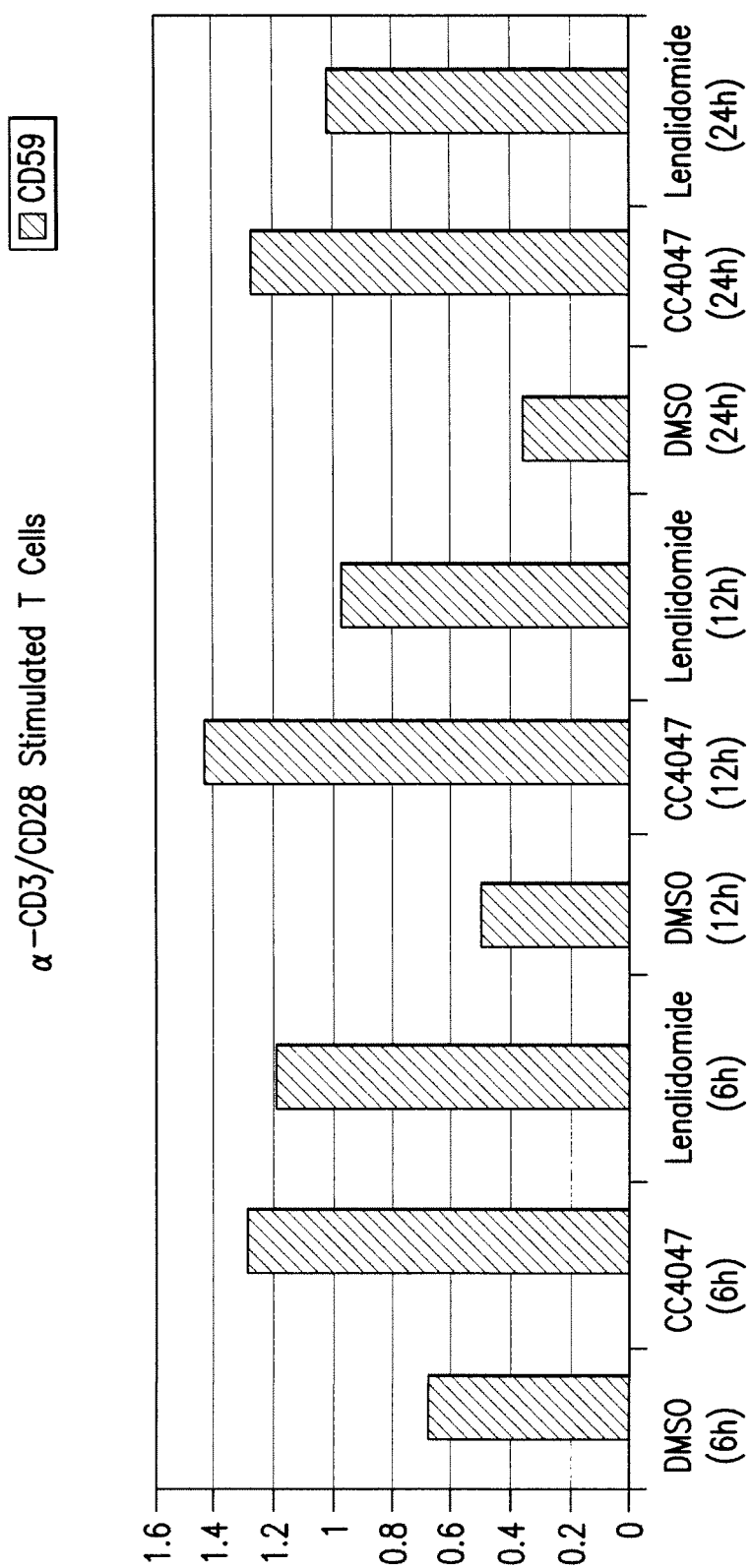
FIG. 3 shows increase in CD59 mRNA levels in α-cd3/cd28 stimulated T cells after treatment with exemplary immunomodulatory compounds, lenalidomide and CC-4047.

As seen in FIG. 3, CD59 mRNA levels in α-cd3/cd28 stimulated t cells show increase after treatment with 3-(4-amino-1-oxo-1,3-dihydro-isoindol-2-yl-piperidine-2,6-dione or 4-amino-2-(2,6-dioxopiperidin-3-yl)isoindoline-1,3-dione.

6.3 Increase in CD59 mRNA Levels in PBMCS

Human PBMCs were isolated from buffy coat from healthy volunteers using ficoll gradient centrifugation. PBMCs were treated with 4-amino-2-(2,6-dioxopiperidin-3-yl)isoindoline-1,3-dione (1 µM) or lenalidomide (10 µM) or vehicle control (0.1% DMSO) for 24 hours, 48 hours, and 72 hours. Cells were harvested and RNA isolated as above. Methods for Affymetrix gene array analysis were as described above.

As seen in FIG. 1, CD59 mRNA levels in PBMC cells show increase after treatment with 4-amino-2-(2,6-dioxopiperidin-3-yl)isoindoline-1,3-dione and lenalidomide.

6.4 Increase in CD59 mRNA Levels in Namalwa Cells

Namalwa cells are cultured in RPM1 supplemented with 10% fetal bovine serum. Cells are treated with vehicle control (0.1% DMSO) or 4-amino-2-(2,6-dioxopiperidin-3-yl)isoindoline-1,3-dione (10 µM) or lenalidomide (10 µM) for 8 hours and 24 hours. Cells are harvested and RNA isolated as described above. Methods for Affymetrix gene array analysis are as described above.

6.5 Increase in CD59 mRNA Levels in CLL Cells

PBMCs are isolated from whole blood from CLL patients (MD Anderson) using ficoll gradient centrifugation. Cells are treated with 4-amino-2-(2,6-dioxopiperidin-3-yl)isoindoline-1,3-dione (1 µM), lenalidomide (10 µM) or N-{[2-(2,6-dioxo(3-piperidyl)-1,3-dioxoisoindolin-4-yl]methyl}cyclopropyl-carboxamide (10 µM) for 24 and 48 hours. Samples from five CLL patients are analyzed individually. Cells are harvested and RNA isolated as described above. Methods for Affymetrix gene array analysis are as described above.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the subject matter claimed and are encompassed by the appended claims.

What is claimed is:

1. A method of treating or managing a disease associated with CD59 deficiency comprising administering to a patient a therapeutically effective amount of an immunomodulatory compound, wherein the immunomodulatory compound is 3-(4-amino-1-oxo-1,3-dihydro-isoindol-2-yl)-piperidine-2,6-dione or 4-amino-2-(2,6-dioxopiperidin-3-yl)isoindoline-1,3-dione, and wherein the disease or disorder is paroxysmal nocturnal hemoglobinuria.

2. The method of claim 1, further comprising administration of an anti-C5 antibody, wherein the anti-C5 antibody is eculizumab, h5G1.1-mAb, h5G1.1-scFv, or a functional fragment of h5G 1.1.

3. The method of claim 2, wherein the anti-C5 antibody is eculizumab.

* * * * *